United States Patent [19]

Holtkamp

[11] Plant 4,557

[45] Jun. 24, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 15,827

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the variety name Alaska having the combined features of large star-shaped white flowers having blue-violet centers and tinged edges, with the flowers being supported on strong upright stems; prominent golden yellow anther cells at center of flower; medium green, large leaves, and vigorous growth habit.

1 Drawing Figure

The present invention comprises a new and distinct cultivar of African violet plant, botanically known as *Saintpaulia ionantha,* and hereinafter referred to by the cultivar name Alaska.

The new cultivar was referred to during the breeding and selection process by the designation B 287/9-97/79, and is a product of a planned breeding program. Alaska is generally characterized by large white star-shaped flowers, which have blue-violet centers and blue-violet tinging at the serrated edges, and prominent yellow anther cells. These traits in combination were not present in previously available commercial cultivars.

The new cultivar was originated from a cross made in a controlled breeding program in Isselburg, Rhineland, Germany. The female, or seed parent was a cultivar designated BESI blue-violet star-shaped, an unpatented cultivar. The male, or pollen parent was XX 104 girl white, also unpatented. The term "girl" is well-known in the industry and refers to cup-shaped green leaves having light green centers.

The new cultivar Alaska was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Alaska which in combination distinguish this African violet as a new and distinct cultivar:

(1) Vigorous growth habit.

(2) Large white-blue violet star flowers with 5-6 petals per flower. The base color of the petals is white, with blue-violet centers and tinging at the edges.

(3) Strong flower stems with 5-7 single flowers per stem.

(4) Medium green leaves, serrated, hairy, velvety.

(5) 8-12 anther cells form a prominent golden yellow flower center.

(6) Flowers do not drop.

The accompanying photographic drawing shows a typical specimen plant of the new cultivar. The colors appearing in the photograph are as true as possible with color illustrations of this type.

Alaska is comparable in certain respects to the cultivar Maine, disclosed in my U.S. Plant Pat. No. 4,350, granted Dec. 19, 1978. Both cultivars have the same maternal parent, but the flowers of Alaska are smaller in diameter and contain more blue-violet in the center, in addition to tinging at the petal edges.

In the following description, color references are made both to the Royal Horticultural Society color chart (RHS) and to the Horticultural Colour Chart (HCC) issued by Wilson Colour Ltd.

Botanical classification: *Saintpaulia ionantha,* Ramat. cv Alaska.

Parentage:

*Male parent.*—XX 104 White Girl.

*Female parent.*—BES I blue-violet star-shaped.

Propagation: The new cultivar holds its distinguishing characteristics through successive propagations by leaf cuttings and by division of shoots.

Plant: From 6 cm to 8 cm tall when grown in pots, and approximately 25 cm in diameter when full grown.

Leaves:

*General form.*—Round to heart-shaped.

*Diameter.*—55-65 mm.

*Texture.*—Soft.

*Aspect.*—Velvety, hairy, serrated.

*Veins.*—Well pronounced, light green, shiny.

*Color (upperside).*—HCC Spinach green, 0960/1.

*Color (underside).*—HCC Sung green, 000 658/2.

*Petiole.*—Light green, strong, hairy.

Flowers:

*Buds.*—Bell-shaped, 7-9 mm before opening, HCC Pastel lavender 440/3.

*Sepals.*—Color: HCC Lettuce green, 861/3. Calyx: flat funnel. Aspect: spear-shaped slightly hairy. Peduncle: short, strong, light green.

Individual flowers:

*Size.*—40-50 mm flat.

*Color (upperside)*—Main color white, center and edges HCC Lobelia blue, from 41/1 to 41/3.

*Color (underside)*.—Main color white, center and edges HCC Lobelia blue 41/3.

*Borne.*—Most of the flowers have 5 petals, a few with 6 petals; all flowers have the large center of anther cells; seed bud pushed through.

*Corolla.*—Main color white, blue-violet symmetrical stripes at the longitudinal edges of the petals from the outside towards the center.

*Arrangement.*—5–7 large, star-shaped flowers on strong slightly bent stems.

*Flowering time.*—6–7 weeks after potting, first flowers appear; 9–10 weeks to a full flowerhead.

Reproductive organs:

*Stamens.*—5–6, close together.

*Anthers.*—10–12 anther cells on short yellow-green stems which are slightly bent, color of anther cells RHS 17C, yellow orange.

*Arrangement.*—Close together.

*Filaments.*—2–3 mm long.

*Styles.*—6–7 mm long, white to light blue-violet dark tip.

*Pollen color.*—RHS 17 D yellow orange.

Roots: Well developed; white when young and active, turning brownish when older.

Disease resistance: No disease problems noticed to date.

General observations: Alaska is a vigorous growing variety with white-blue-violet star-shaped flowers, which, with prominent golden-yellow anther cells, provide an attractive flower bouquet on strong stems, well above the leaves.

I claim:

1. A new and distinct cultivar of African violet, as shown and described, known by the variety name Alaska and characterized by the combined features of large star-shaped white flowers having blue-violet centers and tinged edges, with the flowers being supported on strong upright stems; prominent golden yellow anther cells at center of flower; medium green, large leaves, and vigorous growth habit.

* * * * *

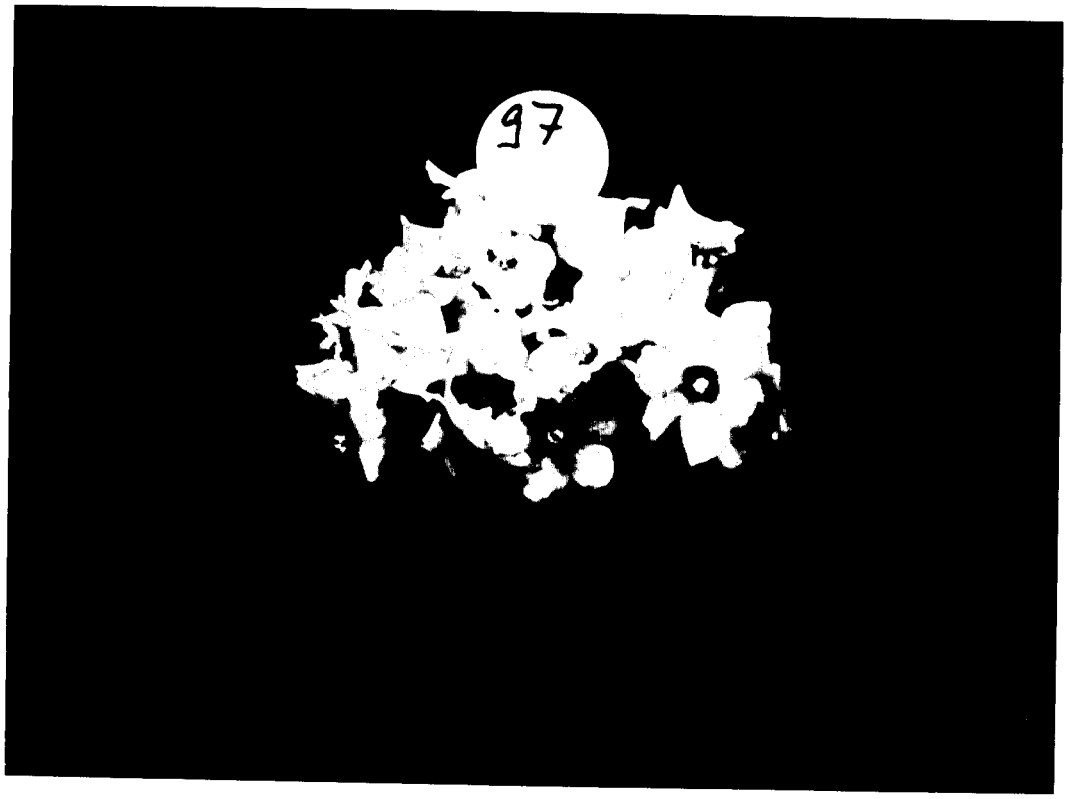
97